US007547520B2

(12) United States Patent
Falcone et al.

(10) Patent No.: US 7,547,520 B2
(45) Date of Patent: Jun. 16, 2009

(54) METHODS TO IDENTIFY PLANT METABOLITES

(75) Inventors: Deane Louis Falcone, Lexington, KY (US); John M. Littleton, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 205 days.

(21) Appl. No.: 11/291,995

(22) Filed: Dec. 2, 2005

(65) Prior Publication Data

US 2006/0084110 A1 Apr. 20, 2006

Related U.S. Application Data

(62) Division of application No. 10/045,677, filed on Jan. 15, 2002, now Pat. No. 6,989,236.

(60) Provisional application No. 60/267,438, filed on Feb. 9, 2001.

(51) Int. Cl.
*G01N 33/60* (2006.01)
(52) U.S. Cl. ...................................................... 435/7.1
(58) Field of Classification Search ........................ None
See application file for complete search history.

(56) References Cited

U.S. PATENT DOCUMENTS

| | | | | | |
|---|---|---|---|---|---|
| 4,717,664 | A | * | 1/1988 | Hara et al. | .................. 435/133 |
| 6,989,236 | B1 | * | 1/2006 | Falcone et al. | ................ 435/7.1 |
| 2003/0092057 | A1 | | 5/2003 | Blume | |

OTHER PUBLICATIONS

Fritze et al 1995, Methods in Molecular Biology vol. 44, Agrobacterium Protocols, Eds K.M.A. Gartland and M.R. Davey, Humana Press Inc. Totowa, New Jersey, pp. 281-294.*
Browning et al 1982, Br. J. Pharmac. 77:487-491.*
Richard A. Houghtling, et al., Molecular Pharmacology: 48:280-287 (1995), Characterization of (±)-[$^3$H]Epibatidine Binding to Nicotinic Sholinergic Receptors in Rat and Human Brain.
Mahanandeeshwar Gattu, et al., Journal of Neuroscience Methods, 63 (1995) 121-125, "A Rapid Microtechnique for the Estimation of Muscarinic and Nicotinic Receptor Binding Parametes Using 96-Well Filtration Plates".
Christopher M. Flores, et al., Journal of Neurochemistry, vol. 69, No. 5, 1997, p. 2216-2219, Differential Requlation of Neuronal Nicotinic Receptor Binding Sites Following Chronic Nicotine Administration.
Csaba Konez et al., Mol. Gen Genet (1986) 204:383-396, The Promoter of $T_L$-DNA Gene 5 Controls the Tissue-Specific Expression of Chimaeric Genes Carried by a Novel Tupe of Agrobacterium Binary Vector.
R. Walden, Methods in Cell Biology, vol. 49, Chapter 32, pp. 455-469, Max-Planck-Institut, Induction of Signal Transduction Pathways Through Promoter Activation.
Klaus Fritze et al., Chapter 25, Methods in Molecular Biology, vol. 44: Agrobacterium Protocols, pp. 281-294, Gene Activation by T-DNA Tagging.
Detlef Weigel et al., Plant Physiology, Apr. 2000, vol. 122, pp. 1003-1013, Activation Tagging in Arabidopsis.
Saubrouk & Russell, Molecular Cloning, A Laboratory Manual, 3rd Edition, Cold Spring Harbor Press NY (2001) pp. 8.20-8.22, Molecular Cloning a Laboratory Manual. 3rd Edition.
Sambrook, Fritsch & Maniatis, Molecular Cloning, A Laboratory Manual, 2nd Edition, Cold Spring Harbor Press, NY (1989), pp. 1.25-1.28, Small-Scale Preparations of Plasmid DNA.
Sambrook, Fritsch & Maniatis, Molecular Cloning: A Laboratory Manual, 2nd Ed., Cold Spring Harbor Press N.Y. (1989), pp. 7.43-7.50, Electrophoresis of RNA Through Gels Containing Formaldehyde.
Sambrook & Russell, Molecular Cloning: A Laboratory Manual, 3rd Edition, Cold Spring Harbor Press N.Y. (2001), pp. 8.46-8.53, Amplification of Cdna Generated by Reverse Transcription of mRNA.
Fritze et al. 1995, Methods in Molecular Biology vol. 44, Agrobacterium Protocols, Eds K.M.A. Gartland and M.R. Davey, Humana Press Inc. Totowa, New Jersey, pp. 281-294.
Browning et al. 1982, Br. J. Pharmac. 77:487-791.
van der Fits et al. 2000, Science vol. 289 Jul. 14, pp. 295-297.

* cited by examiner

*Primary Examiner*—David H Kruse
(74) *Attorney, Agent, or Firm*—McDermott Will & Emery LLP (57) ABSTRACT

This invention provides materials and methods to manipulate the plant genome at the level of single plant cells in culture resulting in the ability to assign metabolic functionality to plant genes involved in the production of biologically active molecules and to create a means of product discovery based on the biosynthetic capacity of plants. The materials to create an activation mutagenesis include incorporation of enhancer sequences from a plant viral promoter at random places in the plant genome via *Agrobacterium* mediated DNA transfer (T-DNA). The usefulness is that genes in the immediate vicinity of the incorporation were activated which allows for immediate screening of the mutagenized plant cells. Additionally, the usefulness includes relevant areas of the genome were flanked by the inserted T-DNA which allows recovery of this area by standard molecular biology techniques. The method includes a procedure for screening large numbers of mutagenized plant cell cultures for activation of a relevant gene on the basis of the desired protein product on the basis of radioligand binding displacement assay.

12 Claims, 11 Drawing Sheets

METHODS TO IDENTIFY PLANT METABOLITES

CROSS REFERENCE TO RELATED APPLICATION

This application is a divisional of U.S. application Ser. No. 10/045,677, filed Jan. 15, 2002 now U.S. Pat. No. 6,989,236, which claims benefit of priority from U.S. Provisional Application Ser. No. 60/267,438, filed Feb. 9, 2001.

BACKGROUND OF THE INVENTION

Plants are sources of drugs and other useful materials. These materials are the products of plant metabolism, which is the total collection of biochemical pathways within a plant. Genes encode the enzymes that function in plant metabolic pathways and regulatory genes, in turn, control the activity of metabolic pathways by directing the expression of entire sets of enzyme-encoding genes specific to a given pathway. It follows that methods to identify any genes that govern the production of such plant metabolites are critical to enable the manipulation of pathways for elevating product yield and for increasing the diversity of these substances. The present invention provides methods to identify, in a relatively efficient and reliable manner, plant-genetic material required for production of metabolites which would ordinarily be difficult to identify. The invention is the realization of the successful merging of two distinct methodologies: activation-tagging mutagenesis and high-throughput screening. The present unique combination of these methodologies results in the ability to assign metabolic functionality to plant genes involved in the production of biologically active molecules and to create a means of compound discovery based on the genetic capabilities of a plant or group of plants.

This invention is therefore based on the following technical developments: 1) methodology which enables propagation and maintenance of mutagenized "microcallus" material in a "library" format in such a way as to permit large scale screening; 2) procedures to nondestructively sample the microcallus; 3) methodology to screen the microcallus sample in a miniaturized high throughput pharmacological screen.

Therefore, the invention is in the field of plant molecular biology, in particular, genetic methods for production and identification of useful compounds.

Identification of plant genes via activation mutagenesis has been used with success previous to the present invention. This technique involves incorporation of enhancer sequences from a plant viral promoter at random places into the plant genome via *Agrobacterium* mediated T-DNA transfer. When applied to single plant cells in culture, the resulting mutants are identified by positive selection, and the gene(s) in the vicinity of the T-DNA insert is cloned. However, elucidation of the effects of mutations in regulatory regions, or downstream effects from a mutagenized gene, are very difficult in cases where no positive selection schemes can be employed. Even with classical activation mutagenesis methods, Walden et al. conclude "this process is involved, labor-intensive and can only be effectively carried out with relatively limited numbers of segregating individuals." Walden et al., Methods in Cell Biology, 49:455-469 (1995).

High-throughput screening has also been utilized in the pharmaceutical field.

Citation of the above document is not intended as an admission that any of the foregoing is pertinent prior art. All statements as to the date or representation as to the contents of these documents is based on subjective characterization of information available to the applicant and does not constitute any admission as to the accuracy of the dates or contents of these documents.

SUMMARY OF THE INVENTION

The present invention provides a method for identifying plant genetic material whose actions cause increased production of a metabolite or metabolites of interest in plant cells, said method comprising causing random integration into the plant genome in plant protoplasts of at least one enhancer-containing T-DNA genetic element harboring sequences to enable bacterial replication and selection; growing said protoplasts to the stage of callus cultures; sampling said callus cultures in such a manner as to retain viability of said clonal cultures; analyzing said samples to identify the callus cultures producing metabolite or metabolites of interest; and isolating and identifying the plant genetic material, the action of which has been stimulated by the enhancer-containing T-DNA genetic element in the sampled, identified callus cultures.

Preferred is a method wherein the plant genetic material, which is identified, is a plant gene whose action causes a plant cell to produce an increased amount of a metabolite or metabolites of interest. More preferred is a method wherein the plant genetic material, which is identified, is a regulatory gene. Also preferred is a method wherein the analysis of callus cultures detects the production of metabolites of interest having pharmacological properties. Most preferred is a method wherein said metabolites are detected via at least one radioligand displacement assay.

Methods of the present invention, which comprises the further step of propagating at least one callus, culture producing said metabolite or metabolites. Most preferred are methods, which involve a tobacco plant.

Most preferred are methods wherein said enhancer sequence is a plant viral enhancer sequence.

Most preferred are methods wherein said enhancer sequence is delivered to the plant via *Agrobacterium tumefaciens*.

Preferred are methods wherein said radioligand is a nicotinic acetylcholine agonist or a nicotinic acetylcholine antagonist. Most preferred is the radioligand [$^3$H]-epibatidine or [$^3$H]-methyllycaconitine.

The present invention provides a method for identifying plant genetic material whose actions cause increased production of a metabolite or metabolites of interest in plant cells, said method comprising co-cultivating plant protoplasts with *Agrobacterium* cells harboring an activation-tagging vector; embedding the plant protoplasts in agarose; transferring the embedded protoplasts to a larger surface area to allow further growth; excising individual, clonal calli resulting from said growth; partially macerating individual samples of tissue from said calli in multi-welled microtiter plates to establish a sample clonal library; removing supernatant liquid fractions from said macerated samples; subjecting said supernatant fractions to radioligand displacement assays to determine if metabolites in the liquid supernatant displace the radioligand; adding growth medium to remaining tissues in the microtiter plate; and isolating and identifying the plant genetic material, the action of which has been stimulated by the action of the activation-tagging vector, from the callus cultures which generated ligand displacement in the radioligand displacement assay.

The present invention provides methods for detecting a metabolite in a plant comprising: causing integration of at least one enhancer-containing T-DNA in a plant protoplast; growing said protoplast to the stage of callus culture; sampling said callus in such a manner so as to retain viability of said callus culture; and detecting a metabolite of interest. Those methods wherein said metabolite is detected via at least one radioligand displacement assay are preferred. More preferred are methods as described which further comprise the step of continuous propagation of at least one stably transformed culture.

In the present invention, methods wherein the plant is a tobacco plant are preferred. Those methods wherein said enhancer sequence is a plant viral enhancer sequence are also preferred. Most preferred are those methods, which utilize a viral enchancer sequence, delivered via *Agrobacterium tumefaciens*.

When the detection means is a radioligand displacement assay, methods wherein said radioligand is a nicotinic acetylcholine agonist or a nicotinic acetylcholine antagonist are preferred. In particular, those methods wherein said radioligand is [$^3$H]-epibatidine are more preferred.

Also provided are methods for detecting a metabolite in a plant comprising: co-cultivating protoplasts with Agrobacterial cells harboring an activation tagging vector; embedding the protoplasts in agarose; transferring protoplasts to a larger surface area to allow further growth; excising individual calli tissue; partially macerating individual calli tissue in a multi-welled microtitre plate; establishing a viable callus library; removing liquid supernatant; adding growth medium to tissues remaining in the microtitre plate; and conducting radioligand displacement assay to determine if a metabolite displaces the radioligand.

For the purposes of the present invention, the term "a" or "an" entity refers to one or more of that entity; for example, "a metabolite" or "a radioligand" or "an assay" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e. combinations) of two or more of the compounds. According to the present invention, an isolated or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawing, which is given by way of illustration only, and thus is not limitative of the present invention.

FIGS. 2A-B.

FIGS. 3A-B.

FIGS. 5A-B.

FIGS. 9A-D.

DETAILED DESCRIPTION OF THE INVENTION

The present invention provides a method for identifying plant genetic material whose actions cause increased production of a metabolite or metabolites of interest in plant cells, said method comprising causing random or directed integration into the plant genome in plant protoplasts of at least one enhancer-containing T-DNA genetic element harboring sequences to enable bacterial replication and selection; growing said protoplasts to the stage of callus cultures; sampling said callus cultures in such a manner as to retain viability of said clonal cultures; analyzing said samples to identify the callus cultures producing metabolite or metabolites of interest; and isolating and identifying the plant genetic material, the action of which has been stimulated by the enhancer-containing T-DNA genetic element in the sampled, identified callus cultures.

Preferred is a method wherein the plant genetic material, which is identified, is a plant gene whose action causes a plant cell to produce an increased amount of a metabolite or metabolites of interest. More preferred is a method wherein the plant genetic material, which is identified, is a regulatory gene. Also preferred is a method wherein the analysis of callus cultures detects the production of metabolites of interest having pharmacological properties. Most preferred is a method wherein said metabolites are detected via at least one radioligand displacement assay.

Methods of the present invention may also comprise the further step of propagating at least one callus culture producing said metabolite or metabolites. Most preferred are methods, which involve a tobacco plant and wherein said enhancer sequence is a plant viral enhancer sequence.

Most preferred are methods wherein said enhancer sequence is delivered to the plant via *Agrobacterium tumefaciens*.

Preferred are methods wherein said radioligand is a nicotinic acetylcholine agonist or a nicotinic acetylcholine antagonist. Most preferred is the radioligand [$^3$H]-epibatidine or [$^3$H]-methyllycaconitine.

In a preferred embodiment, the present invention provides a method for identifying plant genetic material whose actions cause increased production of a metabolite or metabolites of interest in plant cells, said method comprising co-cultivating plant protoplasts with *Agrobacterium* cells harboring an activation-tagging vector; embedding the plant protoplasts in agarose; transferring the embedded protoplasts to a larger surface area to allow further growth; excising individual, clonal calli resulting from said growth; partially macerating individual samples of tissue from said calli in multi-welled microtiter plates to establish a sample clonal library; removing supernatant liquid fractions from said macerated samples; subjecting said supernatant fractions to radioligand displacement assays to determine if metabolites in the liquid supernatant displace the radioligand; adding growth medium to remaining tissues in the microtiter plate; and isolating and identifying the plant genetic material, the action of which has been stimulated by the action of the activation-tagging vector, from the callus cultures which generated ligand displacement in the radioligand displacement assay.

The present invention provides methods for detecting a metabolite in a plant comprising: causing integration of at least one enhancer-containing T-DNA in a plant protoplast; growing said protoplast to the stage of callus culture; sampling said callus in such a manner so as to retain viability of said callus culture; and detecting a metabolite of interest in the event that the metabolite of interest is present. Those methods wherein said metabolite is detected via at least one radioligand displacement assay are preferred. More preferred are methods as described which further comprise the step of propagating at least one daughter culture.

In the present invention, methods wherein the plant is a tobacco plant are preferred. Those methods wherein said enhancer sequence is a plant viral enhancer sequence are also preferred. Most preferred are those methods, which utilize a viral enhancer sequence, delivered via *Agrobacterium tumefaciens*.

When the detection means is a radioligand displacement assay, methods wherein said radioligand is a nicotinic acetylcholine agonist or a nicotinic acetylcholine antagonist are preferred. In particular, those methods wherein said radioligand is [$^3$H]-epibatidine are more preferred.

Also provided are methods for detecting a metabolite in a plant comprising: co-cultivation of protoplasts with Agrobacterial cells harboring an activation-tagging vector; embedding the protoplasts in agarose; transferring protoplasts to a larger surface area to allow further growth; excising individual calli tissue; partially macerating individual calli tissue in multi-welled microtitre plate; removing liquid supernatant; conducting radioligand displacement assay to determine if a metabolite displaces the radioligand; and adding growth medium to tissues remaining in the microtitre plate.

Other methods of transformation include: biolistic bombardment and polyethylene glycol-mediated DNA uptake. Plant cells may also be transformed with other sequences with the ability to cause the activation of genes such as enhancer sequences from different promoters and sequences encoding transcription factors that can function to activate gene expression or from the introduction of populations of genes in order to determine their impact on metabolite production.

The supernatant may be assayed for products of secondary metabolism with radiolabelled ligand binding assays. Preferred ligands are acetylcholine agonists and antagonists. More preferred are $^3$H-methyllycaconitine, $^3$H-spermidine. Most preferred is $^3$H-epibatidine.

Preferred enhancer sequences include tissue-specific promoter enhancers and temporal-specific promoter enhancers. Most preferred is a constitutive plant viral promoter active in plant cells and undifferentiated callus tissue.

Enhancer sequences may be contained within vectors enabling the transfer of said sequences into the plant genome.

The term "antagonist" is intended to refer to that which is understood in the art. In general, the term refers to a substance that interferes with receptor function. Antagonists are of two types: competitive and non-competitive. A competitive antagonist (or competitive blocker) competes with the naturally occurring ligand for the same binding site. In the case of acetylcholine, an example of such an antagonist is bungarotoxin. A non-competitive antagonist or blocker inactivates the functioning of the receptor by binding to a site other than the acetylcholine-binding site.

Specifically, the radiolabeled ligand may bind nicotinic acetylcholine receptors. The preferred radiolabeled ligand is [$^3$H]-epibatidine, a nicotinic cholinergic receptor agonist. Cholinergic receptors play an important role in the functioning of muscles, organs and generally in the central nervous system. There are also complex interactions between cholinergic receptors and the function of receptors of other neurotransmitters such as dopamine, serotonin and catecholamines.

Acetylcholine (ACh) serves as the neurotransmitter at all autonomic ganglia, at the postganglionic parasympathetic nerve endings, and at the postganglionic sympathetic nerve endings innervating the eccrine sweat glands. Different receptors for ACh exist on the postganglionic neurons within the autonomic ganglia and at the postjunctional autonomic effector sites. Those within the autonomic ganglia and adrenal medulla are stimulated predominantly by nicotine and are known as nicotinic receptors. Those on autonomic effector cells are stimulated primarily by the alkaloid muscarine and are known as muscarinic receptors.

The nicotinic receptors of autonomic ganglia and skeletal muscle are not homogenous because they can be blocked by different antagonists. For example, d-tubocurarine effectively blocks nicotinic response in skeletal muscle, whereas hexamethonium and mecamylamine are more effective in blocking nicotinic responses in autonomic ganglia. The nicotinic cholinergic receptors are named the NM and NN receptors, respectively.

Acetylcholine receptors at any or all of the above mentioned locations may be assayed by radiolabeled ligand binding assays in the present invention.

EXAMPLES

The following examples illustrate the present invention without, however, limiting it. It is to be noted that the Examples include a number of molecular biology, microbiology and biochemistry techniques considered to be known to those skilled in the art. Disclosure of such techniques can be found, for example, in Sambrook et al., ibid., and related references.

Example 1

Leaf Protoplast Preparation

Growing Conditions: Tobacco plants (*Nicotiana tabacum* SR1) were grown in sterile culture on MS media (One liter contains: 4.3 g MS basal salt mixture (Sigma), 0.5 g MES (2-[N-Morpholino]ethanesulfonic acid) (Sigma) for buffering, 10 g sucrose. The pH was adjusted to 5.8 with KOH. Media was solidified by adding Phytagel (Sigma) to 0.2%. Sterilization was by autoclaving in Magenta boxes. Magenta boxes contained lids with a vent provided by a 2 cm diameter hole covered with a single 0.45 µm pore size filter disc (Type HA, Millipore) and two pieces of "Micropore" surgical tape (3M). Plants grown for four to five weeks at 24° C. under approximately 110 µmol $m^{-2}s^{-1}$ light intensity were used as a source of leaf material.

Leaf Preparation Procedure: Under sterile conditions, leaf tissue was removed from the plants and cut into approximately 1 $cm^2$ pieces using a sharp scalpel or razor blade. Approximately 5 g of leaf material was added to 20 ml filter-sterilized enzyme solution (1.5% cellulase, 0.5% pectinase, (Sigma)) in K3 plant culture media. K3 media contains 10 ml per liter of the following stock solutions: $NaH_2PO_4$ (3 g/200 ml); $CaCl_2$ (18 g/200 ml); $(NH_4)2SO_4$ (2.7 g/200 ml); $MgSO_4$ (5 g/200 ml); $KNO_3$, (5 g/200 ml); $NH_4NO_3$ (2.7 g/200 ml). Added directly to one liter of K3 media was inositol, 100 mg; xylose, 250 mg; and MES buffer, 2.0 g. In addition, K3 media also contained 10 ml per liter of a micronutrients solution and 1.0 ml per liter of a vitamin solution. The micronutrient solution was prepared by dissolving the following into one liter $H_2O$: $H_3BO_3$, 6.2 g; $MnSO_4\cdot 4H_2O$, 22.3 g; $ZnSO_4.7H_2O$, 10.6 g; KI, 0.88 g; $NaMoO_4\cdot 2H_2O$, 0.25 g; $CuSO_4\cdot 5H_2O$, 0.025 g; and $CoCl_2\cdot 6H_2O$, 0.025 g. The vitamin stock solution was made by dissolving the following in 200 ml $H_2O$: glycine, 400 mg; nicotinic acid, 400 mg; pyridoxin-HCl, 400 mg; thiamin-HCl, 20 mg. 5.0 ml of an Fe-EDTA solution was added from a stock, prepared by dissolving 5.57 g $FeSO_4\cdot 7H_2O$ and 7.45 g $Na_2EDTA$. To prepare K3 containing 0.4M sucrose, 136.92 g sucrose was added. 0.1M sucrose K3 media contains 34.23 g sucrose.

Protoplast Isolation: Leaves were digested overnight (no more than 19 h) by incubation at 26° C. in the dark. The following day, 250 ml beakers were mixed for 10 min on an orbital shaker (approximately 40 rpm), and the solution was passed through a 105 µm mesh sieve by pouring through a filtration apparatus. This was divided into 17×100 mm sterile plastic centrifuge tubes, which were then centrifuged at 2000 rpm in a swinging bucket rotor for 6 minutes at room temperature. Following the centrifugation, protoplasts, which float at the top of the media in the centrifuge tube, were removed from the pelleted debris by aspirating the lower contents of the tube. Protoplasts were washed by addition of 0.4M K3 media and recentrifuged. The protoplasts from these were pooled into one or two single screw cap sterile tubes. After adjusting protoplast cell density, cells were further incubated as 10 ml cultures in standard (60 mm) petri dishes. Dishes were wrapped with parafilm for incubation at 26° C. in the dark for two days.

Example 2

Activation-Tagging Mutagenesis: Protoplast Transformation

Materials: *Agrobacterium tumefaciens* strain GV3101, is described in Koncz and Schell, Mol Gen Genet 204:383-396. 1986, which is incorporated herein by reference in its entirety. The plasmid pPCVICEn4HPT containing the T-DNA tag was used. It was made as described in Fritze and Walden, Methods in Molecular Biology 44:281-294. 1995 and in Walden, Fritze and Harling, Methods in Cell Biology 49:455-469. 1995, which references are incorporated by reference herein in their entirety. pPCVICEn4HPT is derived from the pPCV vector (Koncz and Schell, Mol Gen. Genet 213:285-290, 1986) in which the T-DNA contains four tandemly repeated enhancer elements derived from the 35S RNA promoter of the Cauliflower mosaic virus, a hygromycin resistance marker for protoplast and plant selection and an *E. coli* plasmid sequence that contains an *E. coli* origin of replication and an ampicillin resistance gene.

Procedure: Transformation with the activator T-DNA tag was performed by co-cultivation with *Agrobacterium tumefaciens* harboring the T-DNA tagging element (strain GV3101, plasmid pPCVICEn4HPT). Freshly grown bacterial cells were added directly to six to eight day-old protoplast cultures in a ratio of 100:1 bacteria to protoplast cells. Co-cultivation was conducted at 26° C. in the dark for 48 hr. At the end of the incubation period, protoplasts were washed three times in W5 media by centrifugation in a swing-out rotor at room temperature. W5 media contained NaCl, 9.0 g/liter; $CaCl_2\cdot 2H_2O$, 18.38 g/liter; KCl, 0.373 g/liter; and glucose, 0.90 g/liter. The pH was adjusted to 5.6-6.0, with HCl. The medium was sterilized by autoclavation. Protoplasts were then resuspended in 0.4M K3 media to produce a final concentration of 106 protoplasts per ml. One ml of protoplast suspension was transferred to a standard (100 mm) petri dish and cultured in a final volume of 10 ml of 0.4 M K3 media containing antibiotic selection against *Agrobacterium* cells (cefotaxime 500 µg/ml) as well as the presence of hormones to maintain cells in a dedifferentiated state (auxin (NAA) 1.0 µg/ml and cytokinin (kinetin 0.2 µg/ml). Hygromycin (15 µg/ml) was also added to the incubation media to select for the protoplasts transformed with the activation-tagging vector.

Example 3

Propagation of Protoplasts and Calli

Culturing of Protoplasts: Transformed cells were embedded in 0.3% low gelling temperature agarose in 100 mm petri dishes. K4 media was then added to the petri dishes containing the soft agarose embedded microcalli. Following protoplast embedding, the K4 media was reduced in osmolarity in 0.1M increments, (starting at 0.4M sucrose, ~580 mOsm) on a weekly basis by changing the liquid phase media over the soft agarose embedded cells. "K4" media contains 10 ml per liter of the following stock solutions: $NaH_2PO_4$ (3 g/200 ml); $CaCl_2$ (18 g/200 ml); KCl (58.8 g/200 ml); glutamine (17.54 g/200 ml); asparagine (5.32 g/200 ml); arginine (3.52 g/200 ml); $(NH_4)_2SO_4$ (2.7 g/200 ml); $MgSO_4$ (5 g/200 ml). Added directly to one liter of K4 media is inositol, 100 mg; xylose, 250 mg, and MES buffer, 2.0 g. In addition, K4 media also contains 10 ml per liter of a micronutrients solution and 1.0 ml per liter of a vitamin solution with the same composition as that used for the K3 media as well as 5.0 ml per liter of a Fe-EDTA solution and sucrose to 0.4 or 0.1M.

Transfer to Larger Areas for Additional Growth: Once microcalli were established (usually four to five weeks), they were released from the agarose by gentle maceration and dilution. Microcalli were further cultured by "surface plating" the transformed tissue onto 0.1M K4 media solidified with 0.8% agar in 150 mm dishes. The released microcalli were "re-embedded" in low gelling-temperature agarose and plated to the surface of solidified K4 media agar plates. This results in a 2 mm thick monolayer of embedded microcalli on the plate such that further growth forms an upward protrusion of the calli large enough for physical sampling. Dilutions were empirically made to adjust the number of individual microcalli on each dish to densities sufficient to enable continued growth of the microcalli up to the stage of sampling.

Example 4

Nondestructive Sampling and Library Establishment

The three steps of sampling, establishment of a viable working library and extract preparation of surface-grown macrocalli are combined into a single process to maximize throughput. Surface-embedded microcalli grown to sizes ranging from approximately 0.5 cm to 1.5 cm ("macrocalli") are deemed sufficient for sampling and establishing the master library. Under sterile conditions, petri dishes containing the surface-grown macrocalli are opened and macrocalli are individually sampled using ring forceps (4.8 mm inner ring diameter, Fine Science Tools, Inc. Foster City, Calif.). This ring size enables a section of tissue weighing approximately 50 mg to be sampled. The removed tissue section is placed into the numbered well of a 48-well microtiter plate containing 0.4 ml fresh K4 media including required growth regulators. Once the 48-well dishes are loaded, a maceration pestle, custom made of Delrin™ plastic (12 cm in length×1-cm dia.) with the maceration end machined to a semi-circle (one-half of the 1-cm circular end) is used to partially macerate the tissue in the well of the plate. Partial maceration is conducted to break open a sufficient proportion of the cells within the 50 mg piece of callus tissue to release the cellular contents for analysis and to maintain an amount of this tissue (generally about ⅓ of each callus section) in the well to enable continued growth and recovery. Because the $^3$H-epibatidine displacement assay (below) can be used with K4 callus growth media, recovery and growth of the microcalli within the wells is virtually 100%. Additional media is added to each well to increase the volume to 1.0 ml. 0.65 ml of the 1.0 ml volume of cellular fluid resulting from the partial callus maceration in each well is removed and transferred to standard 1.5 ml micro-centrifuge tubes. After sealing the lids of the 48-well dishes with surgical tape (3M), they are placed in a lighted 26° C. incubator for recovery and growth. The growing calli within the 48-well dishes establishes the working library.

Example 5

Extract Preparation

Micro-centrifuge tubes containing 0.65 ml of cell tissue fluid and K4 growth media are centrifuged at 13,000 rpm for ten minutes at room temperature. The supernatant is removed and placed into clean micro-centrifuge tubes and stored at −80° C. until used for displacement assays.

Example 6

[$^3$H]-epibatidine Screening

Tissue Preparation: Crude membrane preparations from brains of male adult Sprague-Dawley rats were prepared from methods modified after Houghtling R A, Davila-Garcia M I, Kellar K J, Mol Pharmacol 48(2):280-7, 1995, which reference is incorporated by reference herein in its entirety. Following sacrifice by rapid decapitation, the frontal cortex and hippocampus were rapidly dissected and homogenized in ice-cold sucrose buffer (0.32 M sucrose, 1 mM EDTA, 0.1 mM phenylmethylsulfonyl fluoride, 0.01% wt/vol sodium azide; pH adjusted to 7.4) using a polytron tissue homogenizer. The homogenate was centrifuged at 1000×g at 4° C. for 10 min. The pellet was resuspended in sucrose buffer and the centrifugation repeated. The supernatant fractions were combined and the P2 membranes recovered as a pellet after centrifugation 15000×g at 4° C. for 20 min. The pellet was washed twice by resuspension in phosphate buffer (same as above, except 50 mM phosphate substituted for sucrose) and centrifuged at 15000×g at 4° C. for 20 min. The final pellet was resuspended in phosphate buffer. Protein was determined by the BCA Protein Assay kit from Pierce, Rockford Ill. Aliquots were stored at −80° C. until use.

Preparation of membrane homogenates: Fresh tissue (bovine brain) was procured immediately after euthanasia by exsanguination. Alternatively, standards and replication of results were confirmed in male Sprague-Dawley rat cerebrum homogenates derived from animals sacrificed by rapid decapitation. The preparation of these membranes was identical to bovine homogenates. Frontal cortex was blocked, then placed in ice-cold HEPES buffer (50 mM) for 10 min. Tissue was weighed, and 4 ml of "incubation" buffer was added. Tissue was homogenized in a 30 ml vol. glass hand-held tissue homogenizer with a teflon pestle. The crude homogenate was washed 3 times by centrifugation at 35,000×G for 20 min at 4° C. After each centrifugation, the homogenate was re-suspended in fresh, cold buffer. Following final washing, 1 ml aliquots were snap-frozen in liquid nitrogen and stored in a −20° C. freezer until use. Prior to use in binding assays, total protein concentration was determined using a modified Lowry method (Sigma Kit) for membrane bound proteins. Protein concentration effects and protein loss were investigated by preparing aliquots of known dilutions of membrane protein suspension into wells, filtering, and measuring the protein concentration remaining on the plate filters via the Lowry method.

Competition binding: To reduce binding of radiolabel to filters, 0.1% BSA was added to the assay buffer. Membranes were diluted with buffer to yield a final protein concentration of 600 µg/well (2 mg/ml). Membranes were added to the wells of a 96-well microtiter plate and incubated at room temperature with 10 nM [$^3$H]-MLA, and unlabelled ligand or unknown samples (100 µl each). Incubation was halted after 2 hr by the addition of ice-cold buffer. The contents of the microtiter plate were harvested onto a 96 well filterplate using a plate harvester (Packard, Inc). Filters were washed 5× with ice cold buffer and the filterplate dried overnight. Scintillation cocktail was then added to the filters and the entire plate counted using a TopCount™ 96-well plate scintillation counter, Packard Instruments, Meriden Conn.

Procedures for $^3$H-epibatidine binding in 96-well filter plates: All procedures were performed at room temperature, unless noted. Assays were performed in standard (350 µl well volume) 96 well microtiter plates. Nicotine or a sample competitor was added to 8 wells at a time using an 8-channel multipipettor. Crude sample extracts were solubilized using 1N HCl, if necessary. Unknown samples were diluted with incubation buffer (50 mM Tris-HCl, 120 mM NaCl, 5 mM KCl, 1 nM MgCl$_2$, 2 mM CaCl$_2$, pH adjusted to 7.4) 1:10. This dilution allows an approximate weight:volume ratio of 100 mg/ml of unknown sample per well. 100 µl of a competitor was added to each respective well. Non specific binding for epibatidine was determined using 10 mM nicotine competition. Membrane homogenates were thawed on ice and diluted with incubation buffer for final protein concentration of each well equal to 4 mg/ml. Membrane homogenate preparation was added to 8 wells at a time, using 8-channel pipettor. A competitor was incubated within wells for 1 hr. at room temp. Following incubation of competitor, $^3$H-epibatidine (New England Nuclear) was added to each well and incubated for 2 hr. Following incubation, the plate was harvested onto a 96 well GF/B filter plate using a Packard 96 well harvester, and rapidly washed 3× with 350 µl 50 mM Tris-HCl buffer (pH=7.4). The plate was then allowed to dry overnight, then 30 µl MicroScint20™ was added to each well before counting with a Packard Topcount™ 96-well plate scintillation counter. Each well was counted for 2 min. Specific binding in the presence of competitor was converted to percentage of total specific binding of $^3$H-epibatidine alone. Significant differences were calculated from CPM averages using Student's 2 tailed t tests.

Example 7

Results

Screening of Activation-Tagged Microcalli: 4400 activation tagged microcalli were screened in a six month period. This was a 75% increase in efficiency over previous methodologies.

Identification of Microcalli with Significant Alkaloid-Displacing Activity: Two stable cell lines were identified that showed significant alkaloid-displacing activity. One of these, 1402, was examined at the whole plant level and showed a 7.5-fold increase in the level of displacement activity over the wild type in extracts prepared from leaf punches from non-transformed plants. The second identified isolate, 5094, showed displacement activity in callus tissue extracts equivalent to alkaloid levels of several orders of magnitude over the wild-type calli.

Example 8

Isolation and Replication of Activated Genes

Isolation: Molecular genetic techniques are conducted using standard methodologies. The analytical sequence is determined by isolating the plant genomic DNA activated by the T-DNA insert through Southern hybridization analysis, followed by polymerase chain reaction (PCR) to establish the insert number and structure. Cloning of the T-DNA along with flanking genomic plant DNA will depend on the structure of the insert, first utilizing plasmid rescue for single site T-DNA insertions. If there are multiple inserts, then genomic libraries will be prepared and screens conducted on these to obtain genomic clones linked to the T-DNA that contain different plant genomic DNA sequences. Resulting clones can be sorted first by Southern analysis and then functionally by reintroduction into wild-type protoplasts and scoring microcalli for the original phenotype. If necessary, subclones of the recovered flanking plant DNA can be prepared and tested for activity by fusing various fragments downstream of the 35S promoter of the Cauliflower mosaic virus, introducing these back into protoplasts and scoring these cells for the phenotype. Once the putative activated genomic DNA is identified, it is used as a probe to screen cDNA libraries of tobacco. In addition, functional analysis to determine nicotinic alkaloid pathway upregulation can be performed by reverse transcription PCR using oligonucleotide primer specific to the pmt gene of tobacco. This provides early molecular evidence if the alkaloid pathway was induced in callus tissue, for example.

Example 9

Figure 8:
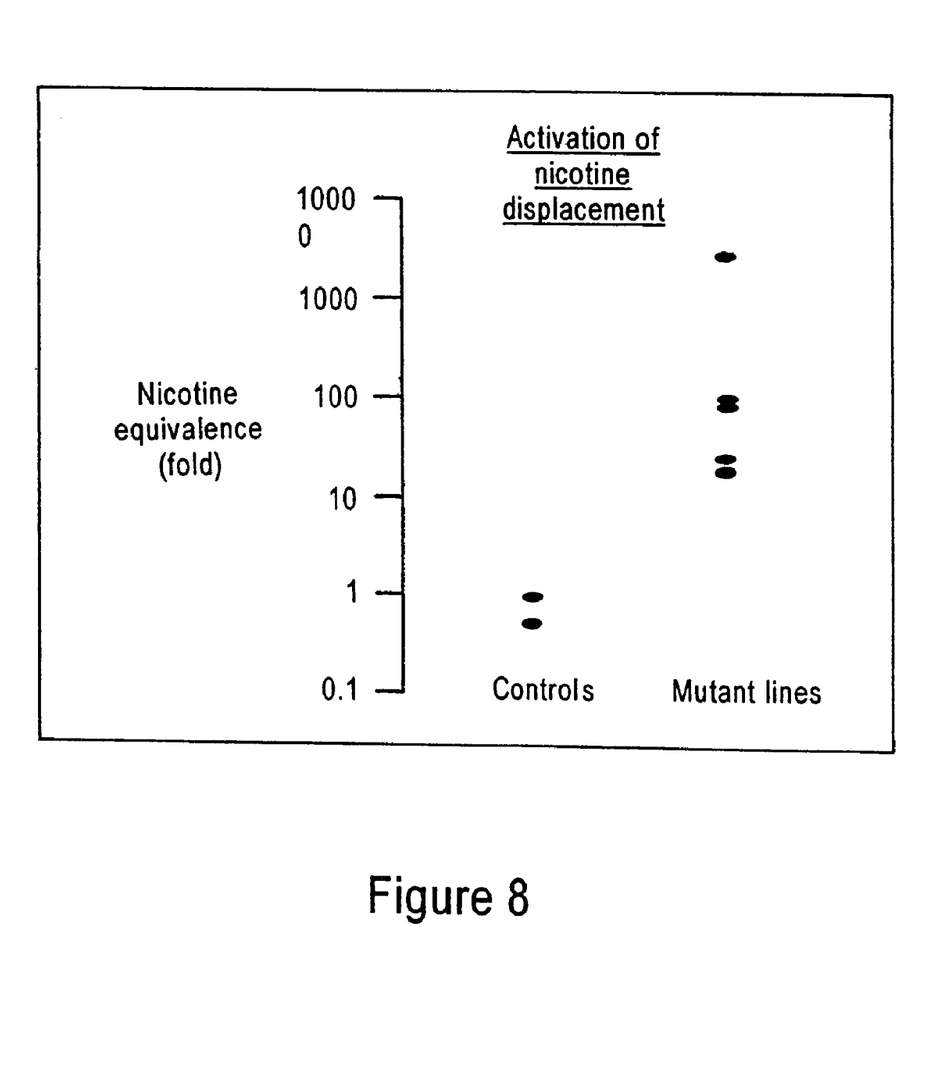
FIG. 8 shows a summary of activities of positive mutant lines and wild-type controls expressed in terms of "nicotine displacement activity" or approximately equivalent to a given concentration of nicotine in the displacement assay. Note log scale on the Y-axis. The upper clone represents activity 10,000 times higher than that found in wild-type calli. This line is no. 7309. The line with the lowest activity (and regenerated and analyzed at the whole plant level) is no. 1402.
Figure 9A:
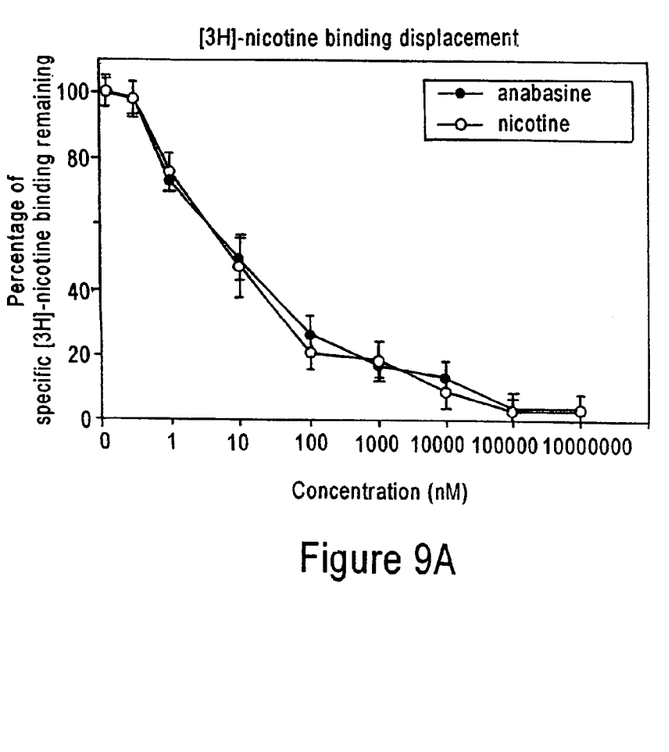
FIGS. 9A and 9B show initial activity characterization by displacement activity of line no. 1402 callus (See discussion text). The pure anabasine alkaoid and pure nicotine alkaloid are used here to standardize the system.
Figure 9B:
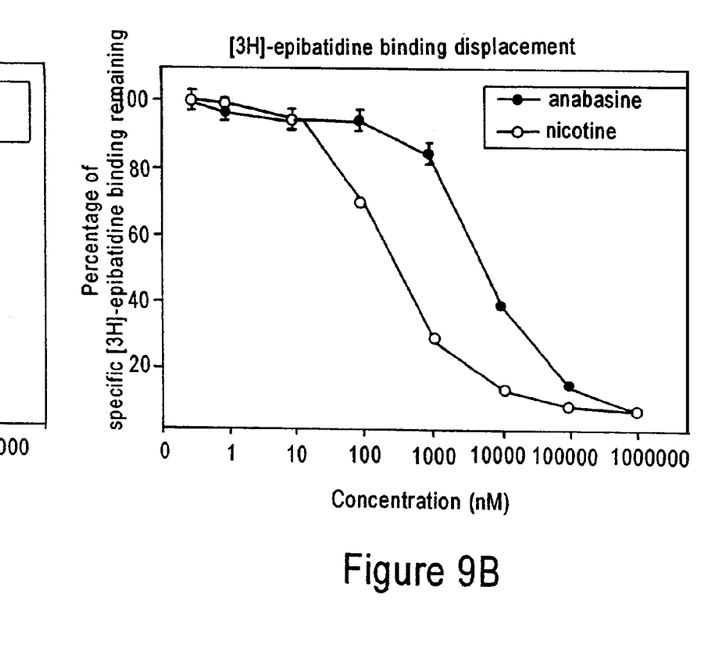
Figure 9C:
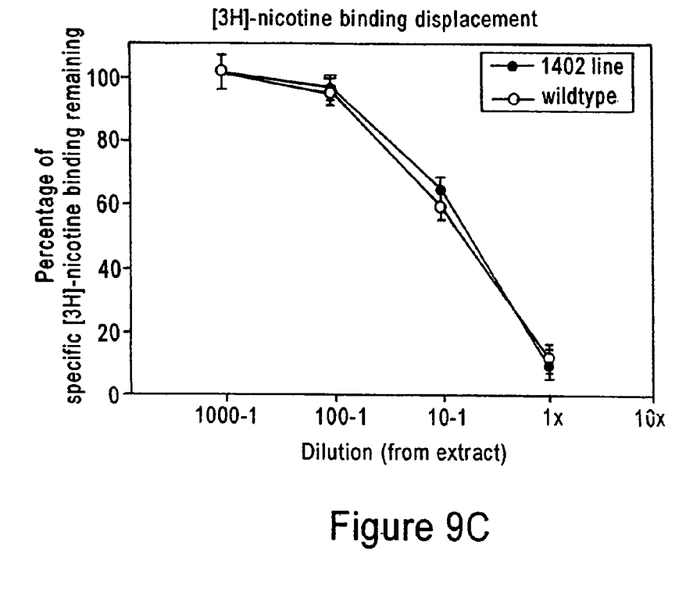
FIGS. 9C and 9D show characterization of crude callus extracts performed in the same way as that in A. This difference in the shape of the profiles indicates that the activity in the 1402 extract is distinct from wildtype and is most likely a compound other than nicotine.
Figure 9D:
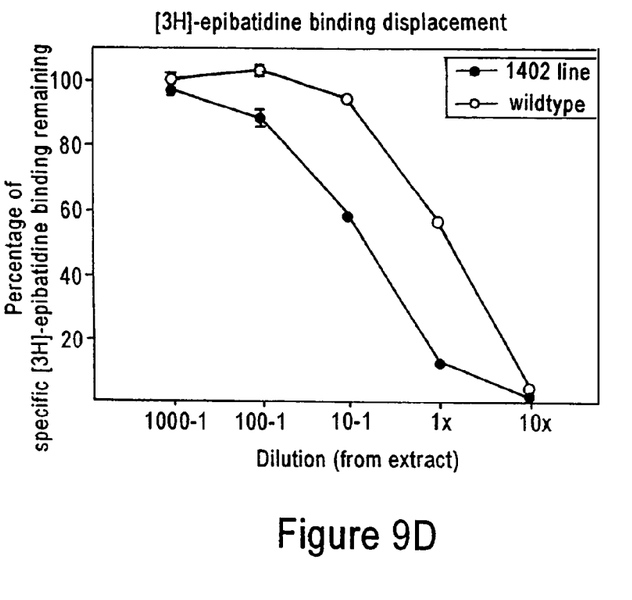

We have prepared extracts from about 8000 clonal cultures and have screened these for [3H]epibatidine-displacing activity. Approximately 12 of these produced activity that met the criteria of being "positive" in the first screen. Of these, only three have met the criteria that daughter cultures should continue to overproduce activity in the screen through several cycles of growth and separation. The extent of the increase in activity varies markedly between these three clones. Thus, the first clone isolated (#1402) producing a compound or compounds with a biological activity in the screen equivalent to a concentration of nicotine an order of magnitude higher than that produced by wild-type cultures (see FIG. 8). A very recent clone (#7309) is producing activity about 10,000× that of wild-type whereas the other clone (#5094) is intermediate between these (FIG. 8). Because we isolated #1402 first we have spent most time characterizing this clone, and the specific findings will be described below.

Figure 1:
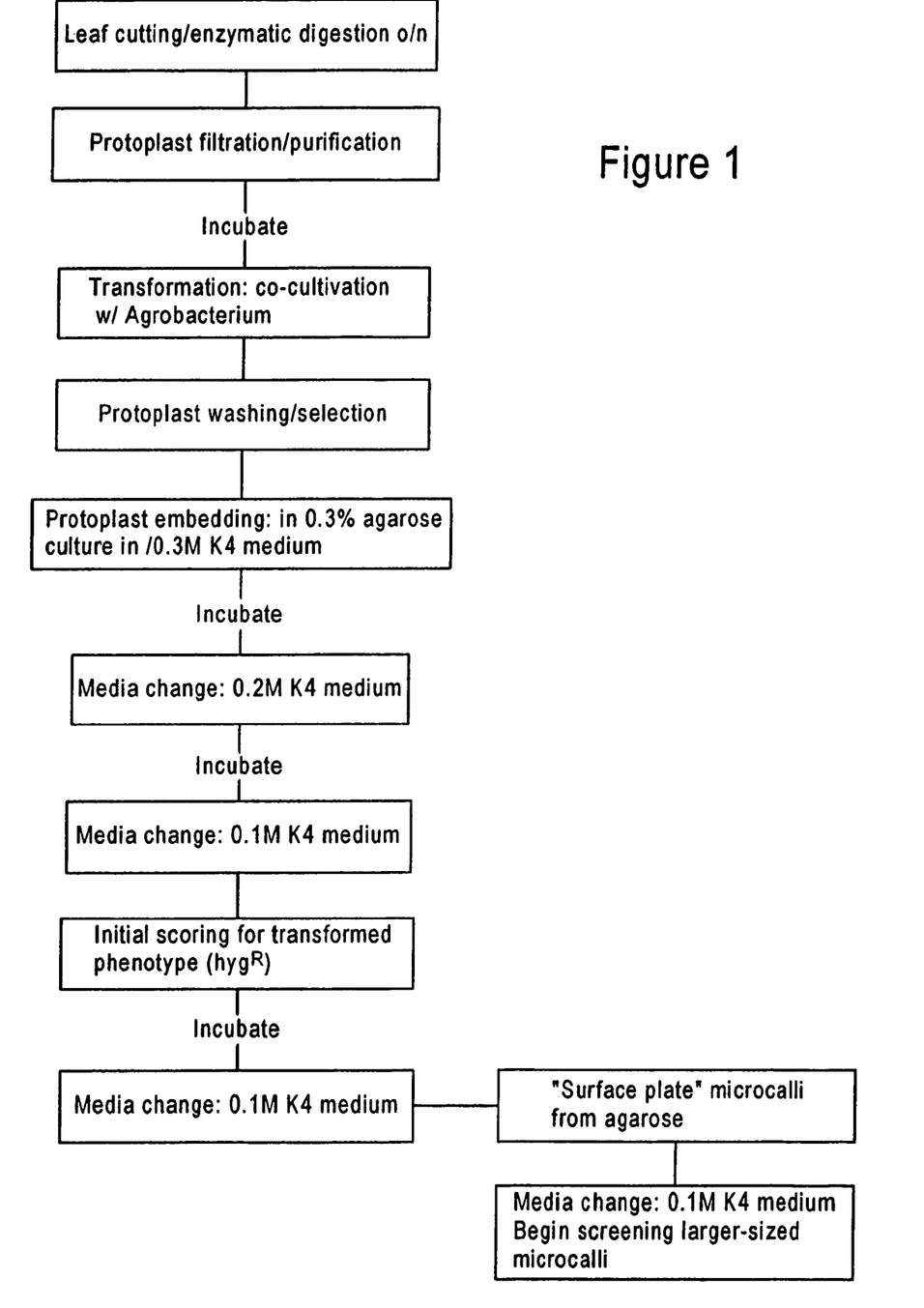
FIG. 1 shows a protoplast isolation and transformation flowchart.
Figure 2A:
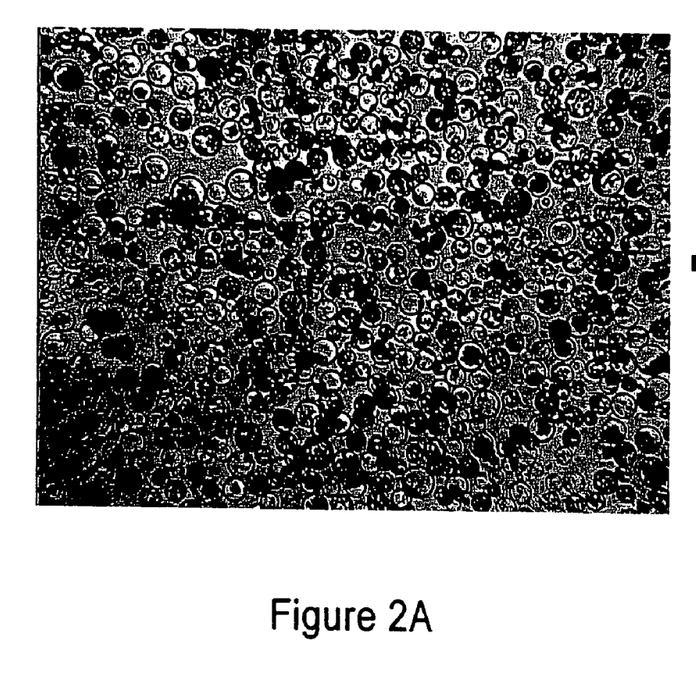
FIG. 2A shows a photograph taken through a bright field microscope (40× magnification) of freshly isolated protoplasts from tobacco leaves two days after isolation. At seven days the protoplasts are co-cultivated with *Agrobacterium tumefacians* (GV3101) to conduct transformation resulting in the insertion of the activation-tagging T-DNA.
Figure 2B:
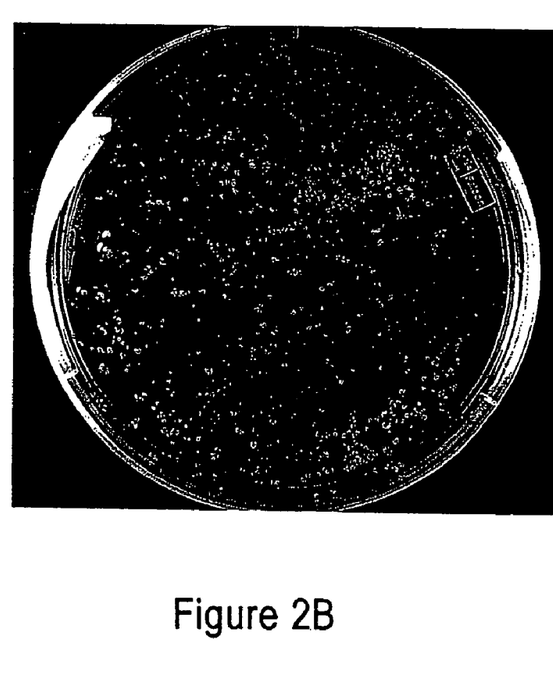
FIG. 2B shows a photograph of a cluster of clonal cells after several steps of incubation, washing, antibiotic selection and embedding of the multiplied protoplasts. The clusters of clonal cells become macroscopic (referred to as "microcalli") as shown in the dish in the right of the figure. Diameter of the petri dish shown is 150 mm.
Figure 3A:
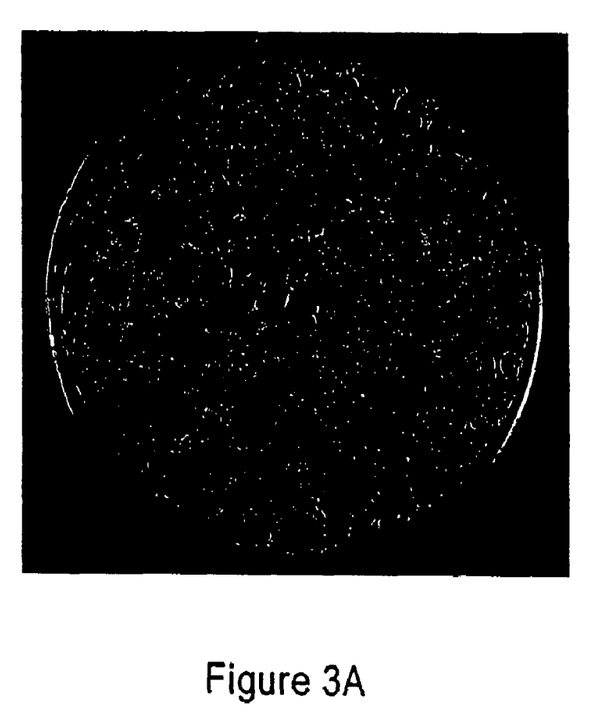
FIG. 3A shows a photograph of a plate of surface-embedded calli after propagation for approximately five weeks (compare to microcalli in FIG. 2). This is an example of the type of density used of mutagenized material used for sampling to conduct the pharmacological assay.
Figure 3B:
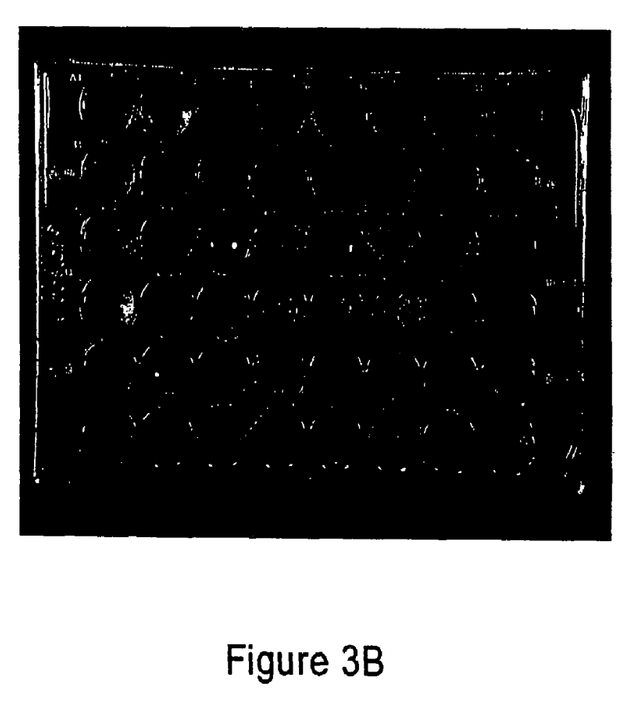
FIG. 3B shows a photograph of a standard 48-well plate showing regrowth of the mutagenized callus tissue after sampling and extract preparation which took place in the same wells approximately three weeks previously.
Figure 4:
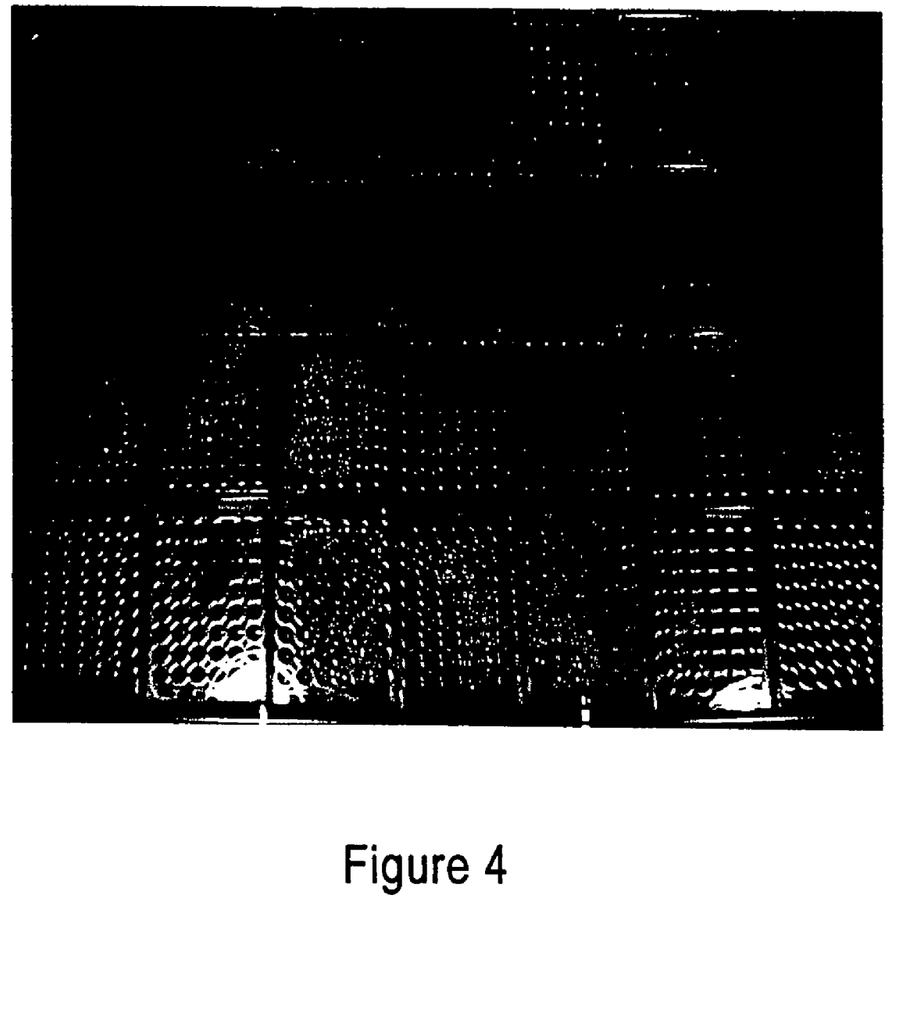
FIG. 4 shows a photograph of an "activation-tagging mutagenesis" (ATM) library that harbors over 1300 individual mutant clones. This illustrates the workability of establishing a viable "master" library developed using the methods described herein.
Figure 5A:
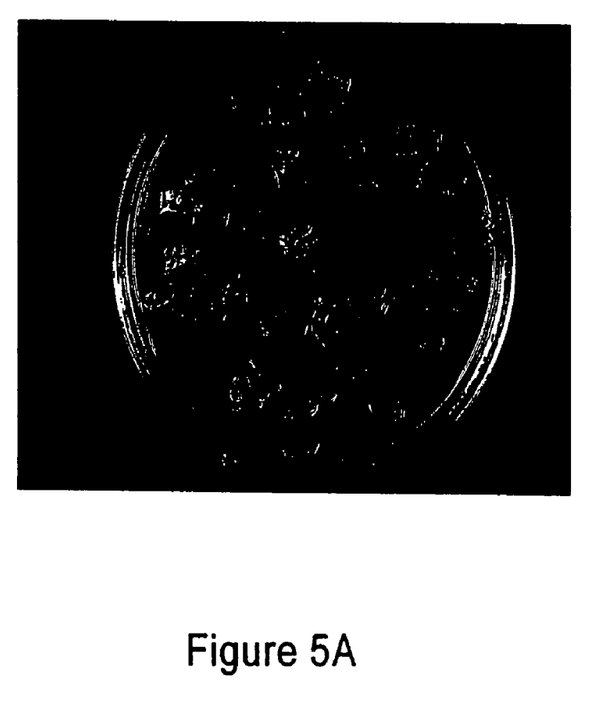
FIG. 5A shows a photograph of an individual screen-positive callus clone that had been physically divided and propagated as approximately 20 clonal pieces of separate callus tissue. This is used for verification of the pharmacological phenotype, as each "daughter" individual is expected to have the same displacement activity as the "parental" tissue.
Figure 5B:
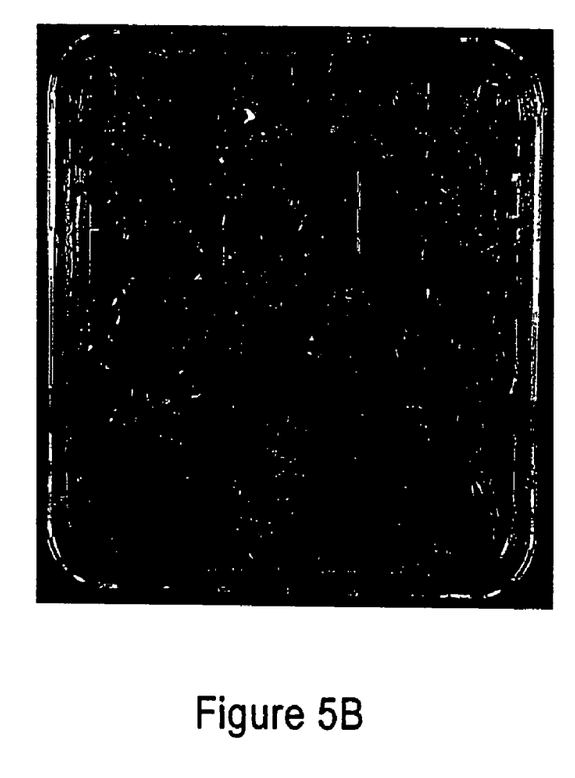
FIG. 5B shows that such pieces are also used for plant regeneration from the calli (right half).
Figure 6:
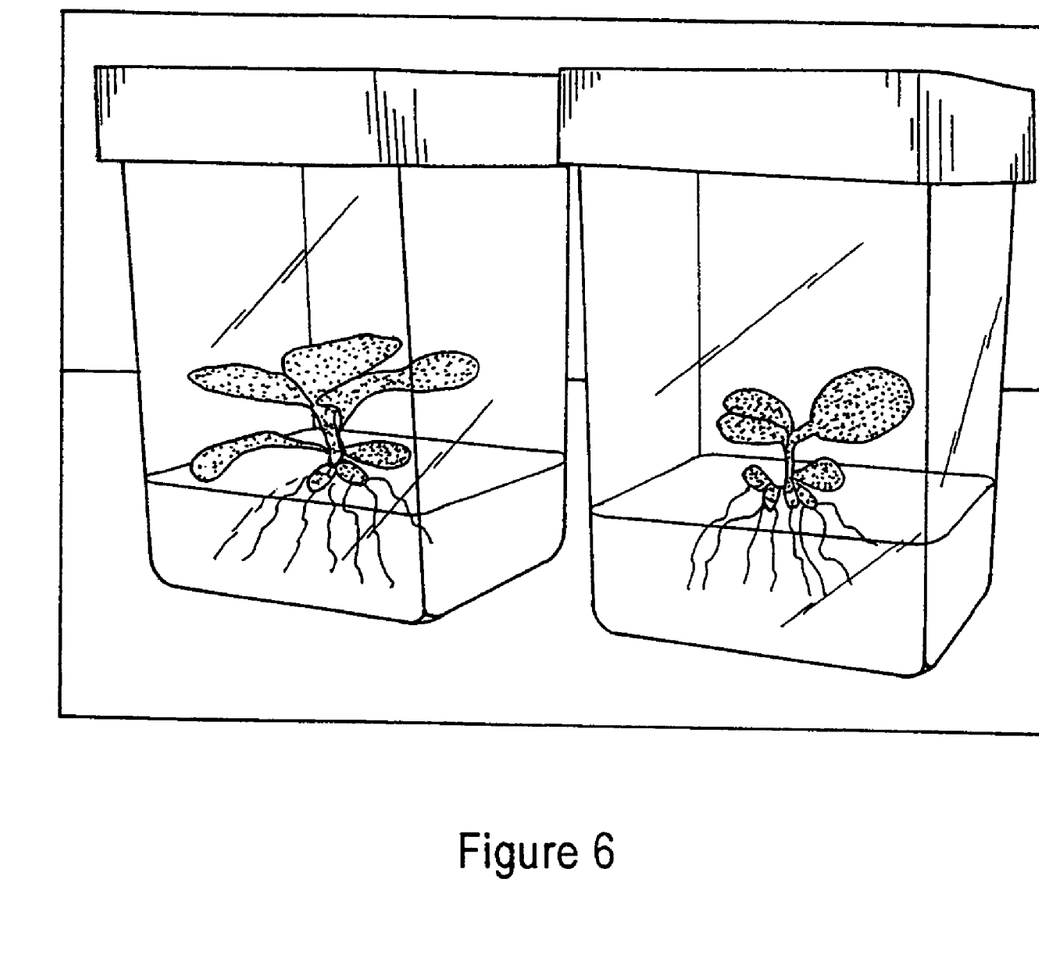
FIG. 6 shows a photograph of plants growing on synthetic media in Magenta boxes that had been regenerated from calli scored as positive in the screen.

The results show that ATM can be used to create a large library of mutant clonal cultures (see FIG. 4) that can be maintained by a small number of research workers. We have also shown that clones in this library can be repeatedly sampled and separated without destroying the individual cultures. Extracts from these cultures can therefore be sampled and screened serially to evaluate whether the genetically produced chemical phenotype is stable. We have also shown that it is possible to adapt pharmacological HTS techniques to evaluation of a clonal library produced by ATM, and that the amplitude of changes in secondary metabolites from wild-type or other control cultures that are produced by ATM can be detected by this HTS. We are thus able to combine ATM and HTS—the first requirement for proof of the Natural Products Genomics concept. Our results using this combination of techniques show that a small number of clones (currently around 1 in 2,700 mutants) can be regarded as stable alterations in genes that increase the synthesis of products with a biological activity similar to nicotine. These products may be nicotine itself, or some other chemical with activity in the screen, at this stage we do not know. Similarly, the genes that have been activated may have an impact on the nicotine metabolic pathway, or be completely unrelated to this. All we know is that they increase the production of natural compounds with potentially useful biological activity that is similar to that of nicotine. In fact, we may well be underestimating the numbers of clones that have this type of value. About 75% of the clones that give a positive result in the first screen eventually fail, sometimes after several generations of positive daughter cultures. Some cultures even recover activity after producing negative data for a while. In some cases, this may indicate that we have activated a gene that regulates the production of the natural product very indirectly, and that its effects can be over-ridden by other genes that may be activated by environmental or developmental factors beyond our control. However, such genes might still be useful as a means of regulating synthesis of the natural product. We have been deliberately conservative in our criteria to avoid the criticisms previously associated with unstable somatic mutations in plant cell culture. Considered together we believe that our results demonstrate that ATM and HTS have the potential to act as a discovery platform for those genes that regulate the synthesis of natural products in plants. As our characterization of clone 1402 has shown (see below) this Natural Products Genomics approach has utility as a drug discovery platform technology.

Clone 1402 has now consistently over-produced activity in the epibatidine displacement screen for about 18 months. This has been in various incarnations of the original clonal material that originated from a single protoplast subjected to ATM (see FIG. 8). Thus, daughter cultures of the original clone continued to overproduce activity in the screen. Some of these cultures were regenerated into intact plants which set seed. Extracts of the seed were screened, and these continued to show greater activity in the screen than wild-type *N tabacum* seed. Plants were grown from this seed and leaf punch extracts from young seedlings showed greater activity in the screen than leaf punches from wild-type seedlings. Leaf protoplasts from these plants were grown to the microcallus level and these microcalli were found to be still overproducing activity relative to wild-type cultures.

Figure 7:
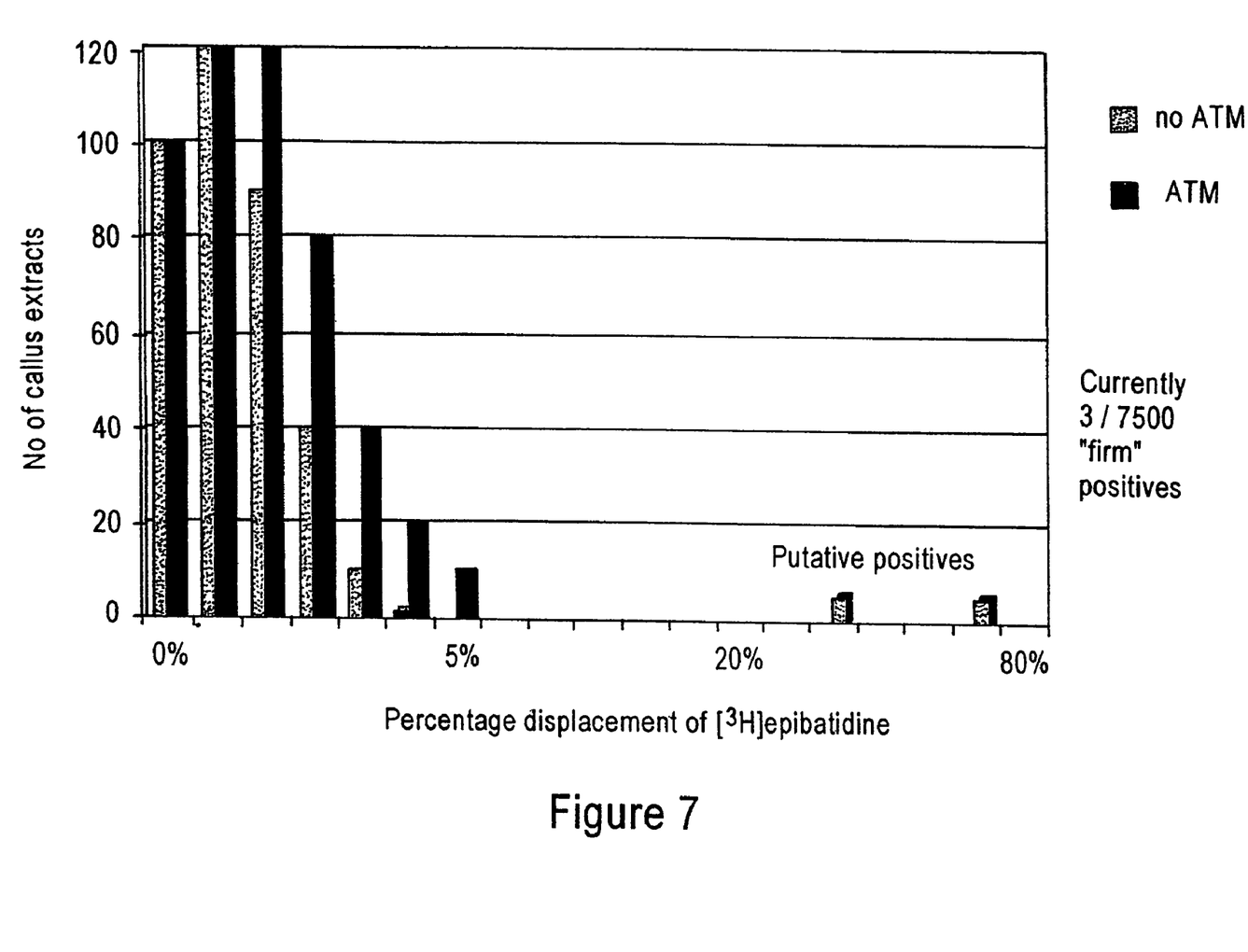
FIG. 7 shows a graph of displacement data of a population of mutant ("ATM") and wild type ("no ATM") using $^3$H-epibatidine as the ligand in the pharmacological screen. Non-mutated samples show average displacement of approximately 3% whereas the ATM population indicates two individuals with greater than 30 and 70% displacement activity, respectively. Note the log scale on the X-axis. These data are typical for many thousands of assays run to date.

The only situation in which clone 1402 was not found to be an overproducer relative to wild-type was in leaf punches from relatively mature plants. At this stage nicotine production is rising rapidly in the wild-type plants and this might well eliminate the difference from the clonal plant. Additionally, assessing the production of nicotine-like alkaloids in leaf punches from mature plants is subject to the Heisenberg principle because leaf damage massively increases the synthesis and transport of nicotine. Our failure to observe a difference in the screen between clone 1402 and wild-type plants at the mature plant stage illustrates the potential difficulties of evaluating differences in natural products in a population of mutant intact plants. Metabolic profiling of the plants at this stage by GC/MS also did not reveal any differences in alkaloid material (see FIG. 7).

Since 1402 consistently overproduces activity in the epibatidine displacement screen it would seem to be a simple matter to establish what compound or compounds it is producing that account for this activity. Unfortunately this is more difficult than would be expected. The problem is one of sensitivity and quantitation. The screen is semi-quantitative at best, but it is extraordinarily sensitive, being easily able to respond to picogram quantities of nicotine in a culture extract. Chemical analytical methods such as GC/MS (as in FIG. 7) are about 1000× less sensitive, and to date we have not accumulated enough clonal culture material to be able to analyze extracts quantitatively for known and novel nicotine-like alkaloids. We have therefore used a combination of pharmacological analysis and separation techniques to investigate extracts of clone 1402 in comparison with extracts from wild-type microcallus.

Nicotine is the most pharmacologically alkaloid in the intact plant, and this alkaloid can be detected by GC/MS in extracts from wild-type cultures. Therefore, the most likely reason for the increased activity in extracts from clonal culture #1402 is that this is producing more nicotine than the wild-type cultures. This does not appear to be the case. Thus, this clonal culture was identified on the basis of greater displacement of epibatidine, a ligand with relative selectivity for alpha3-containing nicAChRs on brain membranes. In contrast, nicotine, and the partial agonist cytisine, have a higher affinity for nicAChRs on brain containing alpha4 subunits. If the active principle in clone #1402 is nicotine it should displace [3H]nicotine or [3H]cytisine from brain membranes to a greater extent than it displaces [3H]epibatidine. In fact the reverse is the case—the same extract from 1402 that is an order of magnitude more effective at displacing epibatidine is no more effective than that from wild-type cultures in displacing nicotine or (see FIG. 9). This suggests that whatever is responsible for the activity has a greater affinity for alpha3-containing nicAChRs, and this is inconsistent with this being nicotine or probably any of the other major alkaloids in tobacco (see below).

FIG. 9 also shows another important pharmacological characteristic of the culture extracts. The dilution/response relation in the screens is very similar to that for pure nicotine. This suggests that the displacement of the respective radioligands is by direct competition for the binding site, rather than by indirect or allosteric effects. This type of interaction suggests an alkaloid that is a structural relative of nicotine rather than a totally different type of compound. For example we know that the cultures produce polyamines (see below) and these compounds can affect nicAChR binding allosterically. The suggestion that the compound in clone 1402 is structurally similar to the known tobacco alkaloids is supported by results from serial fractionation of the extracts from #1402 and wild-type cultures. We compared these fractions for activity in the radioligand binding screens and also compared the recovery in each phase with that of standards representing the major alkaloids present in *N tabacum*. In general, the activity in extracts from #1402 showed a similar distribution to that from wild-type cultures and to that of alkaloid standards (not shown here).

Taken together, all this data is consistent with the production, by clone 1402, of an alkaloidal compound (or compounds) with structural similarity to nicotine, but which bind with high affinity to nicAChRs containing alpha3 subunits. Since none of the major alkaloids in the plant have exactly these characteristics, then we appear to have produced a stable mutation that causes "overproduction" either of a compound that is not normally found in the plant, or one that is normally produced in very small amounts. This finding, and the procedure we used to come to this conclusion, has some implications for drug discovery. Specifically, if the main purpose of this technology is to discover clones that are producing active compounds other than the major active principle in the plant, it is a simple matter to use differential activity in two related screens to do this. Those clones that are simply over-producing the "wild-type compound" will produce a characteristic ratio of activity in the two screens. Those that are producing some product with novel properties will usually produce a ratio of activity that differs from this.

Figure 10:
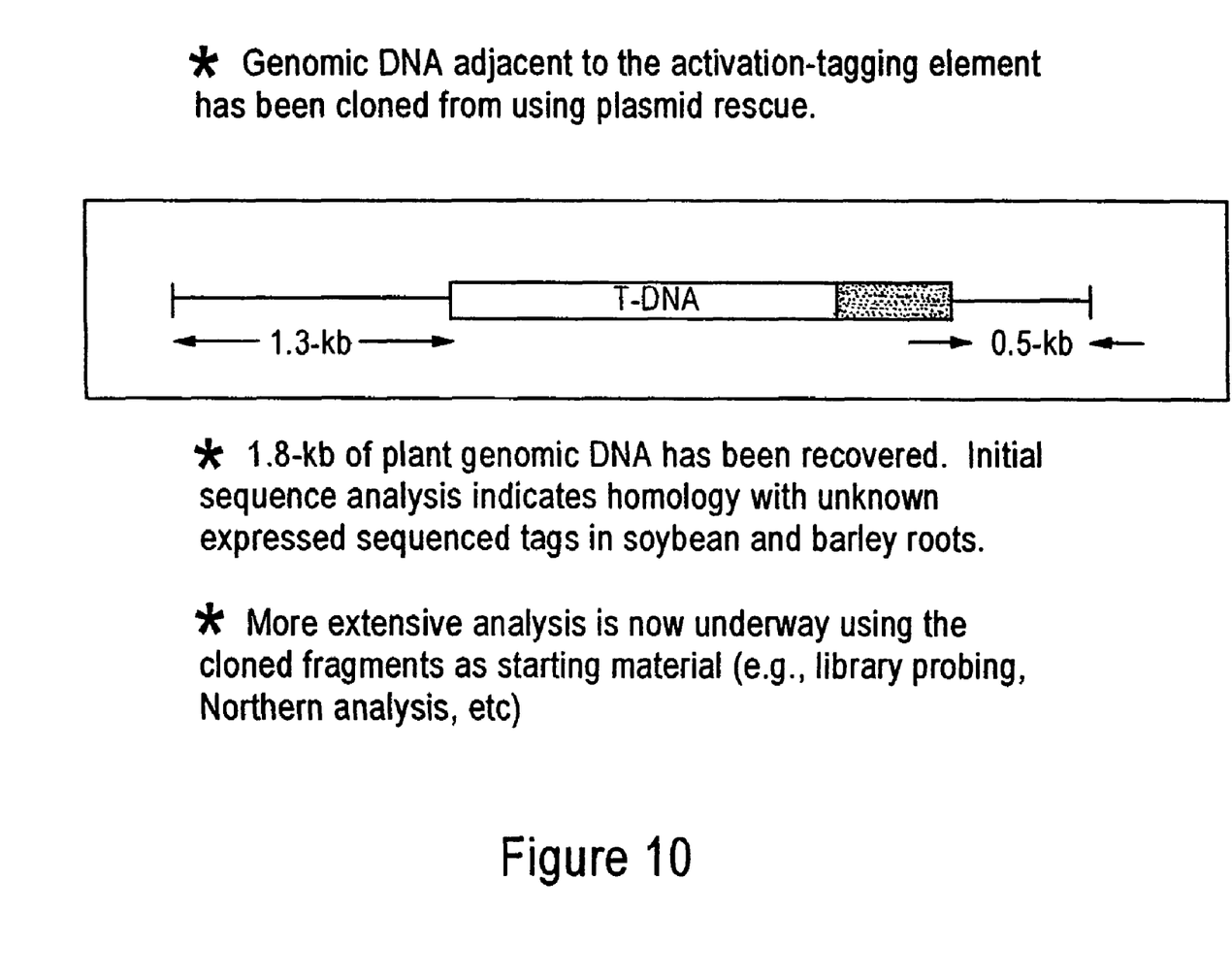
FIG. 10 shows a summary of the molecular characterization of cell line 1402.

Since the T-DNA that has been inserted into the *N tabacum* genome during the ATM procedure is "tagged" with bacterial DNA, it is a relatively simple method to rescue this material together with sections of the plant genes surrounding it. However, this does not guarantee that the piece of plant DNA that is obtained is responsible for the altered chemical phenotype. Thus the influence of the viral enhancer sequences inserted into the genome extends for as much as 10-Kb pairs in each direction from the insert, and it may be any gene within this range that is of value for natural product synthesis. Another potential problem is that there may be more than one insert. The important activation may be in one of these rather than the other or, possibly, it could require both. Fortunately clone #1402 has only one T-DNA insert and we have used plasmid rescue techniques to obtain genomic plant DNA from the region of this insert. To date we have isolated approximately 1.8-Kb pairs of this material (see FIG. 10), which is probably of insufficient length to encode a complete gene. However, the sequence analysis indicates very strongly suggests that the cloned genomic DNA does indeed encode intact genes in that the deduced amino acid sequence from this region reveals some homology with expressed genes when compared with existing gene databanks. In particular, there is homology with expressed sequence tags obtained from a soybean roots that represents a gene of unknown function (FIG. 10). Since the nicotine alkaloids are synthesized in roots, this at least shows the expected tissue specificity.

Those skilled in the art will recognize, or be able to ascertain using no more than routine experimentation, many equivalents to the specific embodiments of the invention specifically described herein. Such equivalents are intended to be encompassed in the scope of the following claims.

We claim:

1. A high throughput screening method for detecting a metabolite of interest in a plant comprising;
   a) causing integration of a T-DNA sequence encoding at least one transcription enhancer and at least one selectable marker gene in a plurality of plant protoplasts;
   b) growing said protoplasts to the stage of callus culture under selective conditions;
   c) removing a tissue sample from the resulting individual callus cultures in such a manner so as to retain viability of said callus cultures;
   d) screening for the metabolite of interest in the tissue sample in the event that the metabolite of interest is present via a radiolabeled ligand binding assay, wherein the radiolabeled ligand binds nicotinic acetyleholine receptors.

2. The method of claim 1, wherein the metabolite of interest is detected.

3. The method of claim 2, which further comprises the step of propagating at least one daughter culture from the callus culture in which the metabolite of interest was detected.

4. The method of claim 1, wherein said plant is a tobacco plant.

5. The method of claim 1, wherein said transcription enhancer is a plant viral transcription enhancer sequence.

6. A method of claim 5, wherein said transcription enhancer is an *Agrobacterium tumefaciens* enhancer sequence.

7. The method of claim 1 wherein said radiolabeled ligand is a nicotinic acetylcholine agonist.

8. The method of claim 1 wherein said radiolabeled ligand is a nicotinic acetylcholine antagonist.

9. The method of claim 4, wherein said metabolite of interest is detected with $^3$H-epibatidinc.

10. The method of claim 1 wherein the tissue sample removed in step (c) is used to establish a library of transformed callus cultures.

11. The method of claim 10 wherein the transformed callus cultures in the library that test positive for the metabolite of interest are rescreened at least one time for the presence of the metabolite of interest by removing a tissue sample from each of said callus cultures in such a manner so as to retain viability of the callus cultures.

12. The method of claim 10 further comprising the step of isolating a gene involved in the production of the metabolite of interest from a callus culture of the library that tests positive for the metabolite of interest after at least one rescreening for said metabolite of interest.

* * * * *